US009376650B2

(12) United States Patent
Notte et al.

(10) Patent No.: US 9,376,650 B2
(45) Date of Patent: Jun. 28, 2016

(54) METHOD OF WATER TREATMENT

(75) Inventors: Patrick Notte, Wavre (BE); Tessa Johnson, Sint Amandsbert (BE); Albert Devaux, Mont-Saint-Guibert (BE)

(73) Assignee: ITALMATCH CHEMICALS SPA, Genoa (IT)

( * ) Notice: Subject to any disclaimer, the term of this patent is extended or adjusted under 35 U.S.C. 154(b) by 1185 days.

(21) Appl. No.: 12/863,962

(22) PCT Filed: Jan. 21, 2009

(86) PCT No.: PCT/EP2009/050668

§ 371 (c)(1),
(2), (4) Date: Feb. 16, 2011

(87) PCT Pub. No.: WO2009/092738

PCT Pub. Date: Jul. 30, 2009

(65) Prior Publication Data

US 2011/0133116 A1 Jun. 9, 2011

(30) Foreign Application Priority Data

Jan. 22, 2008 (EP) .................................... 08100756

(51) Int. Cl.

*G01N 31/00* (2006.01)
*G01N 33/00* (2006.01)
*C11D 3/36* (2006.01)

(52) U.S. Cl.

CPC ................ *C11D 3/361* (2013.01); *C11D 3/364* (2013.01); *C11D 3/365* (2013.01)

(58) Field of Classification Search

CPC .......... C02F 2/12; C02F 2/14; C02F 2103/10; C02F 2103/28; C02F 9/3808; C02F 5/12; C02F 5/15

USPC ............ 252/175, 180, 389.2, 408.1; 210/699, 210/700; 510/401, 402

See application file for complete search history.

(56) References Cited

U.S. PATENT DOCUMENTS

| | | | | |
|---|---|---|---|---|
| 4,079,006 | A | 3/1978 | Mitchell | |
| 4,080,375 | A | 3/1978 | Quinlan | |
| 5,062,962 | A | 11/1991 | Brown et al. | |
| 5,087,376 | A | 2/1992 | Bendiksen et al. | |
| 5,112,496 | A | 5/1992 | Dhawan et al. | |
| 5,263,539 | A | 11/1993 | Salimi et al. | |
| 5,414,112 | A | 5/1995 | Dragisich | |
| 6,022,401 | A | 2/2000 | Tang et al. | |
| 2010/0145066 | A1 * | 6/2010 | Notte et al. | 548/413 |

FOREIGN PATENT DOCUMENTS

| | | |
|---|---|---|
| DE | 141930 | 5/1980 |
| DE | 4131912 | 4/1993 |
| EP | 408297 | 1/1991 |
| EP | 5780304 | 1/1994 |
| EP | 375800 | 4/1994 |
| WO | 0149756 | 7/2001 |
| WO | 03000704 | 1/2003 |
| WO | 2005061782 | 7/2005 |
| WO | WO 2008071692 A2 * | 6/2008 |

OTHER PUBLICATIONS

Kunlin Huang et al, Covalent Bonding of Phosphonates of L-Proline and L-Cysteine to v-Zirconium Phosphate, Eur. J. Inorg. Chem. 2004, 2956-2960.

STN Nov. 16, 1984.

* cited by examiner

*Primary Examiner* — Khanh Tuan Nguyen
(74) *Attorney, Agent, or Firm* — Husch Blackwell LLP

(57) ABSTRACT

A method for securing the use of an aqueous medium under any substantial exclusion of metal ion interference is disclosed. A phosphonic acid compound containing: a selected phosphonate moiety and a moiety selected from a limited number of species; or hydrocarbon chains containing aminoalkylene phosphonic acid substituents; or alkylamino alkylene phosphonic acids containing an active moiety embodying N, O, and S. The technology can, by way of illustration, be used in numerous applications including secondary oil recovery, scale inhibition, industrial water treatment, paper pulp bleaching, dispersant treatment, sequestering application, brightness reversion avoidance and paper pulp treatment.

12 Claims, No Drawings

METHOD OF WATER TREATMENT

This application is a U.S. National Phase Application of International Application PCT Application No. PCT/EP2009/050668, filed on Jan. 21, 2009, which claims the benefit of priority from European Patent Application No. 08100765.0, filed on Jan. 22, 2008. The disclosures of International Application PCT Application No. PCT/EP2009/050668 and European Application 08100765.0 are incorporated herein by reference.

This invention relates to a method of water treatment to thereby substantially inactivate selected metal ions. In particular, the method comprises adding to an aqueous phase of from 0.1 to 100,000 ppm (part per million) of a phosphonate compound having the formula E-B wherein E is selected from: specific organic moieties, termed T; linear or branched hydrocarbon chain moieties having from 6 to $2 \cdot 10^6$ carbon atoms; and moieties comprising N, O and S; and B is represented by a specifically defined phosphonate containing moiety.

The technology can be used beneficially in numerous well known applications based on a predominantly aqueous medium wherein metal ions can adversely interfere with the reactants, the medium, catalysts, the end products and the objective of the intended use of the medium. Examples of such treatments are secondary oil recovery, scale inhibition, industrial water treatment, reverse osmosis, paper pulp bleaching, dispersants, sequestrent and brightness reversion avoidance in paper pulp treatment. Examples of controllable metal ions include earth alkali metal ions such as calcium, strontium, barium and magnesium and metal ions such as iron, chromium, manganese, cobalt, nickel and copper.

The domain of effectively controlling the formation of inorganic deposits, in particular inhibiting the formation of undesirable levels of the like deposits, including frequently calcium carbonate and barium sulphate, in water is well known and has been around for a long time. As one can consequently expect, the relevant art is fairly crowded.

WO 01/49756 discloses scale inhibitors comprising a hydro soluble copolymer consisting of major amounts of styrene sulfonic acid and vinyl sulfonic acid and, optionally, minor levels of non-ionisable monomers. These inhibitor combinations can be used in a squeeze treatment. U.S. Pat. No. 5,112,496 describes compositions and methods for inhibiting oil field scale formation, particularly in high brine environments. Aminomethylene phosphonates containing 2 or more amine moieties, wherein substantially all of the available N—H functions have been phosphonated, are suitable for use. U.S. Pat. No. 4,080,375 pertains to methylene phosphonates of amino-terminated oxyalkylates, having at least two amino groups, and the use thereof as scale inhibitors in marine oil recovery activities as well as their use for chelation in biological systems. As an example, the phosphonates can effectively sequester iron ions within the context of secondary oil recovery by means of water floods.

U.S. Pat. No. 5,263,539 describes method and composition technology useful for controlling and reducing the occurrence of scale in subterranean formations. The inhibitor compositions comprise an amino phosphonic acid and a copolymer of an alkenyl sulfonic acid compound and an ethylenically unsaturated monomer. The phosphonic acid can be represented by bishexamethylene triamine pentamethylene phosphonic acid. GB 2 306 465 pertains to a method of scale inhibition for use in oil field operations where water can contain high concentrations of alkaline earth metal salts such as barium salts. Preferred scale inhibitors can be represented by hydroxyl alkylated phosphonomethyl amines.

U.S. Pat. No. 6,022,401 discloses biodegradable corrosion inhibitors and anti-sealants for use in oil field fluid systems and other industrial water applications. The corrosion inhibitors/anti-sealants are represented by modified poly(aspartic acid) polymers and modified aspartic acid units. The modified aspartic acid can be substituted by selected side chains such as methyl phosphonic acids/salts.

EP 0 408 297 describes scale inhibitors suitable for inhibiting calcium and barium scale formation in aquatic systems in which iron can be present. The inhibitor is represented by a methylene phosphonate, preferably carboxybisnitrilo tetra (methylene phosphonic acid), also known as urea (tetramethylene phosphonic acid). WO 01/85616 divulges a scale- and corrosion-inhibitor for application, inter alia, in water used in oilfield activities, containing, at least, one oxyalkylene unit and one phosphonate unit. The oxyalkylene can be represented by triethylene glycol or tetraethylene glycol. The phosphonate can be represented by vinyl phosphonic acid or vinylidene diphosphonic acid. In a preferred approach, the phosphonate and the oxyalkylene constituents can be reacted to thus yield a single compound for use.

Kulin Huang et al., Eur. J. Inorg. Chem. 2004, 2956-2960, describe the synthesis of functionalized γ-zirconium phosphate-phosphonates based on N-phosphonomethyl-L-proline from proline and N-phosphonomethyl-1,3-thiazolidine-4-carboxylic acid from cysteine. A method for producing N-phosphonomethylglycine by reaction of hexahydrotriazine with triacyl phosphate is described in WO 2003 000704. Along the same lines, DD 141 930 describes the manufacture of monophosphonated amino acids or the esters thereof. The amino acid moiety can, in the final product, be represented by α-alanine, β-alanine, phenylalanine and asparagine. The purpose of the study was the preparation of monophosphonates having one residual N—H function.

DE 41 31 912 discloses mixtures of carboxyalkane aminomethane phosphonic acids prepared by reacting natural proteins, in particular from waste such as e.g. leather, corn and soya, egg white, skimmed and sugar-free milk powder, wool and silk waste, animal hair and other protein wastes. U.S. Pat. No. 5,087,376 discloses a method of inhibiting the formation of scale-forming salts by means of a low level of diphosphonomethyl derivatives of taurine or cysteic acid.

U.S. Pat. No. 5,414,112 discloses N-bis(phosphonomethyl) amino acids and their use to control calcium carbonate scale in contact with industrial process waters. Specific compounds described are N,N-bis(phosphonomethyl)-L-glutamic acid, N,N-bis(phosphonomethyl)-L-serine and N,N,N',N'-bis(phosphonomethyl)-L-lysine. The L-lysine compound is represented by species carrying one phosphonomethyl moiety attached to one amino radical.

WO 2005/061782 describes a method for reducing brightness reversion of mechanical and chemical pulps. In essence, the process comprises the sequence of activating the fibres with an oxidizing agent followed by attaching to the oxidized sites a modifying agent to block the reactivity of the activated sites. U.S. Pat. No. 5,062,962 discloses a principle of inhibiting scale formation in industrial water systems by introducing into the circulating aqueous system a polyepoxy succinic acid. EP 0 578 304 pertains to a process for the bleaching of chemical pulp whereby in the final bleaching stage hydrogen peroxide is applied in the presence of a stabilizing agent whereby the pulp has, preparatory to the hydrogen peroxide treatment, been purified by reducing the manganese content to below 3 ppm.

The art, in essence, aims at adding cumulative functionalities to thus secure additive results without providing remedy to known performance deficiencies, such as within the context of marine oil recovery activities and/or water treatment applications, and/or avoiding multi component systems which are known to exhibit material deficiencies which are inherently attached to such known active combinations.

It is a major object of this invention to provide a beneficial method for scale inhibition capable of effectively limiting scale in aqueous environment under a broad range of conditions including temperature, hardness levels and alkalinity. It is another object of this invention to provide an effective scale control method thereby substantially using a single active scale inhibitor. Another object of the invention aims at providing effective oil scale control without any substantial secondary negatives in relation to e.g. the medium of application. Still another object of this invention aims at providing effective means for water treatment control. Yet another object of this invention concerns a provision of scale control under severe temperature conditions. Still further objects of this invention aim at providing beneficial dispersants, agents for the avoidance of brightness reversion, paper pulp bleaching additives and effective sequestering agents, in particular in relation to heavy metals.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions, and both terms comprise the free acids, salts and esters of phosphonic acids. The term "ppm" stands for "parts per million".

The foregoing and other objects of this invention can now be met by the provision of a method for securing an aqueous medium under substantial exclusion of metal ion comprising a selected phosphonic acid compound. In more detail, the technology herein contemplates adding to the water of from 0.1 to 100000 parts per million (ppm) of a phosphonate compound selected from the group of:

(a) a phosphonate compound of the general formula:

T-B

Wherein B is a phosphonate containing moiety having the formula:

$—X—N(W)(ZPO_3M_2)$

Wherein X is selected from $C_2$-$C_{50}$ linear, branched, cyclic or aromatic hydrocarbon moiety, optionally substituted by a $C_1$-$C_{12}$ linear, branched, cyclic, or aromatic group, which moiety and/or which group can be optionally substituted by OH, COOH, F, OR' and SR' moieties, wherein R' is a $C_1$-$C_{12}$ linear, branched, cyclic or aromatic hydrocarbon chain; and $[A\text{-}O]_x$-A wherein A is a $C_2$-$C_9$ linear, branched, cyclic or aromatic hydrocarbon chain and x is an integer from 1 to 200;

Z is a $C_1$-$C_6$ alkylene chain;

M is selected from H, $C_1$-$C_{20}$ linear, branched, cyclic or aromatic hydrocarbon moieties and from alkali, earth alkali and ammonium ions and from protonated amines;

W is selected from H, $ZPO_3M_2$ and $[V—N(K)]_nK$, wherein V is selected from: a $C_2$-$C_{50}$ linear, branched, cyclic or aromatic hydrocarbon moiety, optionally substituted by $C_1$-$C_{12}$ linear, branched, cyclic or aromatic groups, which moieties and/or groups are optionally substituted by OH, COOH, F, OR' or SR' moieties wherein R' is a $C_1$-$C_{12}$ linear, branched, cyclic or aromatic hydrocarbon moiety; and from $[A\text{-}O]_x$-A wherein A is a $C_2$-$C_9$ linear, branched, cyclic or aromatic hydrocarbon moiety and x is an integer from 1 to 200; and K is $ZPO_3M_2$ or H and n is an integer from 0 to 200;

and wherein T is a moiety selected from the group of:

$MOOC—X—N(U)—;$ (i)

$MOOC—C(X^2)_2—N(U)—;$ (ii)

$MOOC—X—S—;$ (iii)

$[X(HO)_{n'}(N—U)_{n''}]_{n'''}—;$ (iv)

$U—N(U)—[X—N(U)]_{n'''}—;$ (v)

D-S—; (vi)

CN—; (vii)

$MOOC—X—O—;$ (viii)

$MOOC—C(X^2)_2—O—;$ (ix)

NHR"—; and (x)

$(DCO)_2—N—;$ (xi)

wherein M, Z, W and X are as defined above; U is selected from linear, branched, cyclic or aromatic $C_1$-$C_{12}$ hydrocarbon moieties, H and $X—N(W)\ (ZPO_3M_2)$; $X^2$ is independently selected from H, linear, branched, cyclic or aromatic $C_1$-$C_{20}$ hydrocarbon moieties, optionally substituted by $C_1$-$C_{12}$ linear, branched, cyclic or aromatic hydrocarbon groups, optionally substituted by OH, COOH, R'O, R'S and/or $NH_2$ moieties; n', n" and n'" are independently selected from integers of from 1 to 100; D and R" are independently selected from $C_1$-$C_{50}$ linear, branched, cyclic or aromatic hydrocarbon moieties, optionally substituted by a $C_1$-$C_{12}$ linear, branched, cyclic, or aromatic group, which moiety and/or which group can be optionally substituted by OH, COOH, F, OR' and SR' moieties, wherein R' is a $C_1$-$C_{12}$ linear, branched, cyclic or aromatic hydrocarbon moiety; and $A'O\text{-}[A\text{-}O]_x$-A wherein A is a $C_2$-$C_9$ linear, branched, cyclic or aromatic hydrocarbon moiety, x is an integer from 1 to 200 and A' is selected from $C_1$-$C_{50}$ linear, branched, cyclic or aromatic hydrocarbon moiety, optionally substituted by a $C_1$-$C_{12}$ linear, branched, cyclic, or aromatic group, which moiety and/or which group can be optionally substituted by OH, COOH, F, OR' and SR' moieties, wherein R' has the meaning given above; with the further proviso that D can also be represented by H;

(b) linear or branched hydrocarbon compounds having from 6 to $2 \cdot 10^6$ carbon atoms containing amino groups substituted by alkylene phosphonate substituents, and/or $—X—N(W)\ (ZPO_3M_2)$ with respect to the hydrocarbon chain, in either terminal or branched positions whereby the molar ratio of the aminoalkylene phosphonate substituents to the number of carbon atoms in the hydrocarbon chain is in the range of from 2:1 to 1:40 whereby at least 30% of the available NH functionalities have been converted into the corresponding aminoalkylene phosphonate acid; or/and into $X—N(W)(ZPO_3M_2)$ substituted groups; and wherein the alkylene moiety is selected from $C_{1\text{-}6}$; and X, W, Z and M have the same meaning as given above; and (c) alkylamino alkylene phosphonates having the formula:

$Y—[X—N(W)(ZPO_3M_2)]_s$ the structural elements having the following meaning:

X is selected from $C_2$-$C_{50}$ linear, branched, cyclic or aromatic hydrocarbon moieties, optionally substituted by a $C_1$-$C_{12}$ linear, branched, cyclic, or aromatic group, which moiety and/or which group can be optionally substituted by OH, COOH, F, OR', $R^2O[A\text{-}O]_x—$ wherein $R^2$ is a $C_1$-$C_{50}$ linear, branched, cyclic or aromatic hydrocarbon moiety, and SR' moieties, wherein R' is a $C_1$-$C_{50}$ linear, branched, cyclic or aromatic hydrocarbon moiety, optionally substituted by $C_1$-$C_{12}$ linear, branched, cyclic or aromatic hydrocarbon groups, said moieties and/or groups can be optionally substituted by COOH, OH, F, OR' and SR'; and $[A\text{-}O]_x\text{-}A$ wherein A is a $C_2$-$C_9$ linear, branched, cyclic or aromatic hydrocarbon moiety and x is an integer from 1 to 200;

Z is a $C_1$-$C_6$ alkylene chain;

M is selected from H, $C_1$-$C_{20}$ linear, branched, cyclic or aromatic hydrocarbon moieties and from alkali, earth alkali and ammonium ions and from protonated amines;

W is selected from H, $ZPO_3M_2$ and $[V—N(K)]_nK$, wherein V is selected from: a $C_2$-$C_{50}$ linear, branched, cyclic or aromatic hydrocarbon moiety, optionally substituted by $C_1$-$C_{12}$ linear, branched, cyclic or aromatic groups, which moieties and/or groups can be optionally substituted by OH, COOH, F, OR', $R^2O[A\text{-}O]_x$— wherein $R^2$ is a $C_1$-$C_{50}$ linear, branched, cyclic or aromatic hydrocarbon moiety, and SR' moieties; and from $[A\text{-}O]_x\text{-}A$ wherein A is a $C_2$-$C_9$ linear, branched, cyclic or aromatic hydrocarbon moiety and x is an integer from 1 to 200;

K is $ZPO_3M_2$ or H and n is an integer from 0 to 200; and

Y is a moiety selected from $NH_2$, NHR', $N(R')_2$, NH, N, OH,

OR', S, SH, and S—S wherein R' is as defined above with the proviso that when Y is OH or OR', X is, at least, $C_4$; and s is 1 in the event Y stands for $NH_2$, NHR', $N(R')_2$, HS, OR' or OH; s is 2 in the event Y stands for NH, S or S—S; and s is 3 in the event Y stands for N.

In one aspect of the method herein, the precursor for Y is selected from: $NH_3$; $NH_2R$; $NH(R')_2$; $OH^-$; HOR; $Na_2S$; thiourea; and $Na_2S_2$.

In the definition of X, $X^2$, D, R', R'', A, U, M and V, the $C_x$-$C_y$ linear or branched hydrocarbon moiety is preferably linear or branched alkane-diyl with a respective chain length. Cyclic hydrocarbon moiety is preferably $C_3$-$C_{10}$-cycloalkane-diyl.

Aromatic hydrocarbon moiety is preferably $C_6$-$C_{12}$-arene-diyl. When the foregoing hydrocarbon moieties are substituted, it is preferably with linear or branched alkyl of a respective chain length, $C_3$-$C_{10}$-cycloalkyl, or $C_6$-$C_{12}$-aryl. All these groups can be further substituted with the groups listed with the respective symbols.

More and particularly preferred chain lengths for alkane moieties are listed with the specific symbols. A cyclic moiety is more preferred a cyclohexane moiety, in case of cyclohexane-diyl in particular a cyclohexane-1,4-diyl moiety. An aromatic moiety is preferably phenylene or phenyl, as the case may be, for phenylene 1,4-phenylene is particularly preferred.

In preferred embodiments, the individual moieties in the phosphonate reaction partner of the (c) component are selected as follows: X is $C_2$-$C_{30}$ or $[A\text{-}O]_x\text{-}A$; V is $C_2$-$C_{30}$ or $[A\text{-}O]_x\text{-}A$; wherein for both, X and V are independently selected, A is $C_2$-$C_6$ and x is 1-100; $R^2$ is $C_1$-$C_{30}$; Z is $C_1$-$C_3$; M is H or $C_1$-$C_6$; and n is 1-100. In yet another more preferred embodiment, the individual moieties in the phosphonate reaction partner of the (c) component are selected as follows: X is $C_2$-$C_{12}$ or $[A\text{-}O]_x\text{-}A$; V is $C_2$-$C_{12}$ or $[A\text{-}O]_x\text{-}A$; wherein for both, X and V are independently selected, A is $C_2$-$C_4$ and x is 1-100; $R^2$ is $C_1$-$C_{12}$; Z is $C_1$; M is H or $C_1$-$C_4$; and n is 1-25.

M is selected from H, $C_1$-$C_{20}$ linear, branched, cyclic or aromatic hydrocarbon moieties and from alkali, earth alkali and ammonium ions and from protonated amines.

In more detail, the essential phosphonate compound herein can be neutralized, depending upon the degree of alkalinity/acidity required by means of conventional agents including alkali hydroxides, earth alkali hydroxides, ammonia and/or amines. Beneficial amines can be represented by alkyl, dialkyl and tri alkyl amines having e.g. from 1 to 20 carbon atoms in the alkyl group, said groups being in straight and/or branched configuration. Alkanol amines such as ethanol amines, di- and tri-ethanol amines can constitute one preferred class of neutralizing agents. Cyclic alkyl amines, such as cyclohexyl amine and morpholine, polyamines such as 1,2-ethylene diamine, polyethylene imine and polyalkoxy mono- and poly-amines can also be used.

Preferred species of the reaction partner T in phosphonate compounds (a) herein are selected from:

(i): caprolactam or 6-amino hexanoic acid; 2-pyrrolidone or 4-amino butanoic acid; and lauryl lactam or 12-amino dodecanoic acid;

(ii): glutamic acid; methionine; lysine; aspartic acid; phenylalanine; glycine; and threonine;

(iv): 2-ethanol amine; 6-amino hexanol; 4-amino butanol; di-(2-ethanolamine); dipropanolamine; 2-(2-aminoethoxy) ethanol; and 3-propanol amine;

(v): diaminotoluene; 1,6-hexamethylene diamine; 1,4-butane diamine; and 1,2-ethylene diamine;

(x): methylamine; ethylamine; propylamine; butylamine; hexylamine; heptylamine; octylamine; nonylamine; decylamine; dodecylamine; aniline; and $C_{12}$-$C_{22}$ fatty amines including linear and, branched species; and (xi) phthalimide; succinimide; and maleimide.

In another embodiment, preferred species of the reaction partner T can be selected from the group of (iii), (vi), (viii) and (ix). Specifically preferred examples of the reaction partner T can be selected from:

(iii): thioglycolic acid; and cysteine;

(vi): methylthiol; ethylthiol; propylthiol; pentylthiol; hexylthiol; octylthiol; thiophenol; thionaphthol; decylthiol; and dodecylthiol;

(viii): 3-hydroxy propanoic acid; 4-hydroxy butanoic acid; 5-hydroxy pentanoic acid; and 2-hydroxy acetic acid; and (ix): tartaric acid; hydroxysuccinic acid; and α-hydroxy isobutyric acid.

Specific and preferred embodiments of the (b) alkylene phosphonic acids can be represented by species wherein the hydrocarbon compound in (b) containing amino groups is selected from: poly(amino) alkanes;

poly(allyl) amines;

poly(vinyl amines); and poly(ethylene imines), branched or linear or combinations thereof whereby the alkylene phosphonates acids are represented by $C_{1\text{-}6}$ phosphates and whereby X is $C_2$-$C_{30}$ or $[A\text{-}O]_x\text{-}A$.

Individual and preferred species of the (b) compounds are selected from the group of:

4-aminomethyl 1,8-octane diamine hexa(methylene phosphonic acid);

4-aminomethyl 1,8-octane diamine hexa(alkylene imino bis(methylene phosphonic acid));

poly[vinylamine bis(methylene phosphonic acid)];

polyethylene imine poly(alkylene imino bis(methylene phosphonic acid));

polyethylene imine poly(methylene phosphonic acid);

poly[vinylamine bis(alkylene imino bis(methylene phosphonic acid))]; and poly[vinylamine bis(methylene phosphonic acid)].

One or more, preferably one to five, phosphonates of the invention are used in the method of the invention.

Scale formation, such as carbonate and sulphate scales, can be a major problem in oil field production facilities that, can result in a significant well productivity decline. This can, in particular, apply when sea water is injected into the oil bearing formation to compensate e.g. for a loss in gas pressure. As a result of the presence of important quantities of barium and calcium ions in the down-hole formation water, calcium sulphate and especially barium sulphate and strontium sulphate can become a major problem in the operation of the well. Whereas sulphate scales prevail upon seawater injection during the enhanced oil recovery treatment, milder pH conditions, prevailing closer to the surface, pressure differences and high temperatures in the down-hole formation usually lead to the formation of mixtures of carbonate and sulphate scale. The scale inhibitors shall therefore exhibit performance over a broad range of conditions such as can occur in the oil wells and production facilities. The inhibitor can be introduced into the oil bearing formation by any suitable treatment including a "squeeze" treatment. In general such a method for oil recovery requires injecting into a marine oil well an aqueous solution of the phosphonic acid scale inhibit of this invention in a usual level of from 0.1 to 100000 ppm. Frequently, the production oil well activity is stopped and the inhibitor solution is injected into the oil well formation. It was established that the scale inhibitors in accordance with this invention can be used effectively and singly. The squeeze treatment generally consists of injecting a scale inhibitor solution into the wellbore of the producing well to place the inhibitor into the formation. The scale inhibitor released from the formation is present, in the return water, in a concentration of, at least, 0.1, usually at least 0.5, frequently from 10 to 100 ppm to thus exhibit effective scale control and consequently secure oil well production continuity with levels of inhibitor means reduced by one order of magnitude compared to actually prevailing practice.

In more detail, a beneficial method for oil recovery can be done by injecting into marine oil wells an aqueous solution of the phosphonic acid compound of the invention in a level of from 0.1 to 100000 ppm. The method can be conducted by continuously injecting into the well an aqueous solution of from 0.1 to 800 ppm of the phosphonic acid compound. The continuous injection frequently means that the scale inhibitor solution is injected into the water injection well. However, it is understood that the continuous injection can also apply to the surroundings of the production well such as the well-head arrangement including under-water equipment for example pumps and pipes. The scale inhibitors of this invention can also be used in squeeze oil recovery methods. Such squeeze method comprises, in sequence: stopping the production wellbore activity; introducing through the production wellbore the aqueous treatment solution containing the phosphonic acid scale inhibitor in a level of from 100 to 100000 ppm; injecting sea water through the production wellbore to place the scale inhibitor within the targeted area of the formation; restarting the oil extraction activity; and producing return fluids, containing oil and return water, through the production wellbore.

In one aspect of the invention, the method can generate appreciable benefits for reducing the susceptibility of materials, such as lignocellulosic materials, to unwanted brightness reversion, in particular to brightness reversion caused by light or heat. The brightness reversion problem well-known in the relevant domain and can be caused by light, in particular UV light, heat, moisture and chemicals. The reversion can translate in reduced reflectivity, particularly in blue light. This reversion, or yellowing, can vary upon the type of pulp used, the raw material used, the production and after treatment methods used. The method of this invention aims at eliminating the known reversion problems to thus yield superior color stability. The inventive method thus can provide, resulting from the use of the inventive phosphonates to the aqueous medium, superior color properties. While not wishing to be bound by any structural hypothesis, it is believed that contrary to the principles underlying reversion control in accordance with the art, the present method is unexpectedly and beneficially controlled through the interaction of the phosphonate/metal ion/reactive site on the bleached compound. The inventive phosphonate is, for bleach reversal avoidance purposes, generally used in levels from 1 to 10000 ppm. Preferred usage ranges require from 5 to 5000 ppm, more preferably from 50 to 1000 ppm of the phosphonate of this invention. The pulp can be used in common art established concentrations in such aqueous medium, e.g. from 0.1 to 10% based of the treatment medium.

In another aspect, the inventive method contemplates treatment of water to inhibit and control the nuisance attached to scale formation. To that effect, the phosphonic acid of this invention is introduced into an industrial water system in levels which can broadly and preferably range from about 0.1 up to about 10000 ppm, usually from about 0.1 to about 1000 ppm frequently from about 1 to about 200 ppm and preferably from 20 to 200 ppm.

In yet another aspect, the method herein can be used beneficially in connection with paper pulp bleaching broadly. Paper pulp bleaching technology is well established and has been used for a long time. The phosphonates serve to stabilize and enhance the performance of the paper pulp bleaching agents used. The phosphonates can be used beneficially in sub-additive levels of e.g. from 1 to 5000 ppm, preferably of from 10 to 2000 ppm.

The method herein can also be used for dispersant purposes. In particular, the phosphonates herein can serve as effective dispersants and thus reduce the viscosity of phyllosilicate in slurries and aqueous medium in general. The dispersant moieties, such as the phosphonate groups, can increase dispersion and exfoliation properties of the said silicates and consequently decrease the viscosity. To that effect the phosphonates herein are preferably used in low levels, frequently in the range up to 10000 ppm starting from e.g. 1 ppm, or differently expressed in a range possible of from 0.01 to 3% based on the level of the phyllosilicates.

The method can also beneficially serve for the sequestering of undesirable metal ions which can be present in very low levels e.g. 1-500 ppm or higher. The phosphonates herein can beneficially serve for effectively hindering such undesirable metal ions to thus reduce the level of free metal ions to sub ppm levels.

In a further aspect of the invention, there is provided the use of one or more phosphonate compound as described above for deactivating metal ions in an aqueous medium, where the one or more phosphonate compound is added to the aqueous medium in an amount of from 0.1 to 100 000 ppm.

To deactivate as used herein means to suppress an adverse effect of the metal ions on the aqueous medium, its components or intended use, such as scale formation, increased viscosity, or unwanted brightness reversion in pulp.

Accordingly, the use for deactivating metal ions in an aqueous medium includes the use as scale inhibitor, dispersant, exfoliating agent, sequestering agent and/or stabiliser.

The aqueous medium comprising one or more phosphonate compounds of the invention is preferably applied in oil production, such as secondary oil recovery, industrial water treatment, reverse osmosis, or paper pulp treatment, such as paper pulp bleaching.

The invention is further illustrated by the following examples.

EXAMPLES

Throughout the example section, the following abbreviations are used.

PIBMPA stands for propyl imino bis(methylene phosphonic acid)

EIBMPA stands for ethyl imino bis(methylene phosphonic acid)

AMODHMPA stands for 4-aminomethyl 1,8-octane diamine hexa(methylene phosphonic acid)

HEIBMPA stands for 2-hydroxy ethyl imino bis(methylene phosphonic acid)

The preparation of phosphonate species which can be used in the invention herein is illustrated in the following synthesis examples.

1. "6-Amino Hexanoic Acid PIBMPA" (Mixture of Mono and Bis Alkylation Product)

Solution 1 is prepared by mixing 22.63 g (0.2 moles) of ϵ-caprolactam with 50 ml of water and 64 g (0.8 moles) of a 50% NaOH solution in water and heated for 3 hours at 100° C. A slurry is prepared by mixing 117.3 g (0.4 moles) of 96% pure 3-chloro propyl imino bis(methylene phosphonic acid) and 150 cc of water. 64 g (0.8 moles) of 50% NaOH solution in water diluted to 150 ml with water are gradually added to this slurry between 5 and 10° C. Solution 2 so obtained is mixed with Solution 1 between 8 and 10° C. At the end of the addition 16 g (0.2 moles) of 50% NaOH solution in water are added before heating the resulting mixture to 105° C. for 6 hours. $^{31}$P NMR analysis of the crude reaction mixture shows 68% molar hexanoic acid 6-imino bis[propyl 3-imino bis (methylene phosphonic acid)]; 15% molar hexanoic acid 6-amino propyl 3-imino bis(methylene phosphonic acid) and 9% molar 3-hydroxypropyl imino bis(methylene phosphonic acid).

2. "11-Amino Undecanoic Acid PIBMPA" (Mixture of Mono and Bis Alkylation Product)

Slurry 1 is prepared by mixing at room temperature of 40.26 g (0.2 moles) of 11-amino undecanoic acid with 75 ml of water and 64 g (0.8 moles) of a 50% NaOH solution in water. Slurry 2 is prepared by mixing 117.3 g (0.4 moles) of 96% pure 3-chloro propyl imino bis(methylene phosphonic acid) and 150 cc of water. To this slurry 64 g (0.8 moles) of 50% NaOH solution in water diluted to 150 ml with water are gradually added between 5 and 10° C. Solution 2 so obtained is mixed with Slurry 1 between 8 and 10° C. At the end of this addition 24 g (0.3 moles) of 50% NaOH solution in water are added to the reaction mixture along with 2 g of KI before heating to 90° C. for 6 hours. $^{31}$P NMR analysis of the crude reaction mixture shows 54% molar undecanoic acid 11-imino bis[propyl 3-imino bis(methylene phosphonic acid)] and 16% molar undecanoic acid 11-amino propyl 3-imino bis (methylene phosphonic acid).

3. "2-(2-Amino Ethoxy) Ethanol PIBMPA" (Mixture of Mono and Bis Alkylation Product)

Solution 1 is prepared by mixing at room temperature 21.03 g (0.2 moles) of 2-(2-amino ethoxy) ethanol with 75 ml of water and 80 g (1 mole) of a 50% NaOH solution in water. Slurry 1 is prepared by mixing 117.3 g (0.4 moles) of 96% pure 3-chloro propyl imino bis(methylene phosphonic acid) and 150 cc of water. To this slurry 48 g (0.6 moles) of 50% NaOH solution in water diluted to with water 120 ml are gradually added between 5 and 10° C. Solution 2 so obtained is mixed with Solution 1 between 8 and 10° C. At the end of this addition 16 g (0.2 moles) of 50% NaOH solution in water are added and the resulting mixture heated to 90° C. for 5 hours. $^{31}$P NMR analysis of the crude reaction mixture shows 55% molar 2-(2-imino ethoxy) ethanol bis[propyl 3-imino bis(methylene phosphonic acid)]; 19% molar 2-(2amino ethoxy) ethanol propyl 3-imino bis(methylene phosphonic acid) and 16% molar of the corresponding azetidinium salt.

4. "Glycine PIBMPA" (Mixture of Mono and Bis Alkylation Product)

Solution 1 is prepared by mixing at room temperature 15.02 g (0.2 moles) of glycine with 75 ml of water and 96 g (1.2 moles) of a 50% NaOH solution in water. Slurry 1 is prepared by mixing 117.3 g (0.4 moles) of 96% pure 3-chloro propyl imino bis(methylene phosphonic acid) and 150 cc of water. To this slurry 48 g (0.6 moles) of 50% NaOH solution in water diluted to 100 ml with water are gradually added between 5 and 10° C. Solution 2 so obtained is mixed with Solution 1 between 5 and 10° C. At the end of this addition 8 g (0.1 moles) of 50% NaOH solution in water are added to the mixture which is heated to 105° C. for 5 hours. $^{31}$P NMR analysis of the crude reaction mixture shows 67.4% w/w glycine bis[propyl 3-imino bis(methylene phosphonic acid)]; 2.2% w/w glycine propyl 3-imino bis(methylene phosphonic acid) and 3% w/w of the corresponding azetidinium salt.

5. "Imino Bis (EIBMPA)" (Mixture of Mono and Bis Alkylation Product)

Solution 1 is prepared by mixing between 5 and 8° C. 111.4 g (0.4 moles) of 96% pure 2-chlor ethyl imino bis(methylene phosphonic acid); 300 ml of water and 30 g (0.375 moles) of a 50% NaOH solution in water. Solution 2 is prepared by mixing 130 g (1.625 moles) of 50% aqueous sodium hydroxide with water to get a final volume of 250 ml. Ammonia solution is prepared by mixing 13.6 g (0.8 moles) of 25% ammonia solution in water with 200 ml of water. Solutions 1 and 2 are gradually added to the ammonia solution with good stirring between 8 and 12° C. This mixture is heated to 80° C. for 5 hours. $^{31}$P NMR analysis of the crude reaction mixture shows 56.2% w/w imino bis[ethyl 2-imino bis(methylene phosphonic acid)]; 22.2% w/w amino ethyl 2-imino bis(methylene phosphonic acid) and 11.8% w/w of the nitrilo tris [ethyl 2-imino bis(methylene phosphonic acid)].

6. "'Glycine EIBMPA" (Mixture of Mono and Bis Alkylation Product)

A glycine solution is prepared by mixing at room temperature 7.51 g (0.1 moles) of glycine with 30 ml of water and 8 g (0.1 moles) of a 50% NaOH solution in water. Slurry 1 is prepared by mixing 55.72 g (0.2 moles) of 96% pure 2-chloroethyl imino bis(methylene phosphonic acid) and 150 cc of water. To this slurry 15 g (0.1875 moles) of 50% NaOH solution in water diluted to 100 ml with water are gradually added between 5 and 10° C. Solution 1 is prepared by diluting 53 g (0.6625 moles) of 50% NaOH in water to a total volume of 110 ml. Solution 1 and slurry 1 are gradually added under stirring to the glycine solution between 8 and 12° C. At the end of this addition 4 g (0.25 moles) of 50% NaOH solution in water are added to the mixture which is heated to 100° C. for 5 hours. $^{31}$P NMR analysis of the crude reaction mixture shows 74.5% w/w glycine bis[ethyl 2-imino bis(methylene phosphonic acid)]; 7.1% w/w glycine ethyl 2-imino bis(methylene phosphonic acid) and 4.8% w/w of the 2-hydroxy ethyl imino bis(methylene phosphonic acid)

7. 4-Aminomethyl 1,8-Octane Diamine Hexa(Methylene Phosphonic Acid)

173.5 g (1 mole) of 4-aminomethyl 1,8-octane diamine were mixed under stirring with 492 g (6 moles) of phosphorous acid, 413.87 g (4.2 moles) of 37% hydrochloric acid and 200 ml of water. The resulting mixture is heated up to 110° C. 541.52 g of 36.6% aqueous (6.6 moles) formaldehyde were added in 300 minutes while maintaining the reaction temperature around 113° C. Upon completion of the formaldehyde addition, the reaction mixture is heated for an additional 60 minutes at 114° C. $^{31}$PNMR analysis of the crude product shows 93.2% of 4-aminomethyl 1,8-octane diamine hexa(methylene phosphonic acid).

8. Poly[Vinyl Amine Bis(Methylene Phosphonic Acid)]

222.67 g (1 mole based on the monomer unit) of a 32.2% w/w polyvinyl formamide (Lupamin 4500 from BASF) were mixed under stirring with 164 g (2 moles) of phosphorous acid, 221.71 g (2.25 moles) of 37% hydrochloric acid and 50 ml of water. The resulting mixture was heated up to 110° C. 168 ml of 36.6% aqueous (2.2 moles) formaldehyde was added in 120 minutes while maintaining the reaction temperature between 108 and 110° C. Upon completion of the formaldehyde addition, the reaction mixture was heated for an additional 60 minutes at 105° C. $^{31}$PNMR analysis of the crude reaction product showed the presence of 60% of polyvinyl amine bis(methylene phosphonic acid) in the reacted product mixture.

9. 2-Hydroxy Ethyl Imino Bis(Methylene Phosphonic Acid)

111.48 g (0.4 mole) Of 96% pure 2-chloroethyl imino bis(methylene phosphonic acid) (CEIBMPA) were mixed under stirring with 300 ml of water. 30 g of a 50% aqueous solution of sodium hydroxide (0.375 mole) was diluted with water to 100 ml and added, under stirring below 10° C., to the CEIBMPA aqueous solution. This mixture was then added over a period of 160 minutes to 162 g (2.025 moles) of 50% sodium hydroxide under good stirring at a temperature between 95° C. and 100° C. Heating was further continued for 60 minutes at 100° C. $^{31}$P NMR of the crude reaction product showed the presence of 88.3% of the hydroxy homologue of CEIBMPA; the corresponding cyclic phosphonate ester is absent from the crude product.

10. Polyethylene Imine Poly(Propyl Imino Bis(Methylene Phosphonic Acid))

146.65 g (0.50 mole) of 96% pure 3-chloro propyl imino bis(methylene phosphonic acid) were added under stirring over 100 minutes to a mixture of 29.25 g of linear polyethylene imine (Mw=423, 0.66 mole based on $—CH_2—CH_2—NH_2$ unit) with 160.8 g (2.01 moles) of 50% sodium hydroxide and 100 g of water while maintaining the temperature between 35° C. and 40° C. When addition was complete, the mixture was heated at reflux for 7 hours. $^{31}$P NMR analysis of the crude product indicated 92% of polymer bound propyl imino bis(methylene phosphonic acid) with 7% of the 3-hydroxy propyl imino bis(methylene phosphonic acid) (HPIBMPA).

11. Polyethylene Imine Poly(Propyl Imino Bis(Methylene Phosphonic Acid))

146.65 g (0.50 mole) of 96% pure 3-chloro propyl imino bis(methylene phosphonic acid) were added under stirring over 100 minutes to a mixture of 19.5 g of linear polyethylene imine (Mw=423, 0.44 mole based on $—CH_2—CH_2—NH_2$ unit) with 160.8 g (2.01 moles) of 50% sodium hydroxide and 100 g of water while maintaining the temperature between 35 and 40° C. When addition was complete, the mixture was heated at reflux for 7 hours. $^{31}$P NMR analysis of the crude product indicated 93% of polymer bound propyl imino bis (methylene phosphonic acid) with 5% of the hydroxy propyl imino bis(methylene phosphonic acid) (HPIBMPA).

12. "6-Amino Hexanoic Acid EIBMPA" (Mixture of Mono and Bis Alkylation Product)

Solution 1 is prepared by mixing 22.63 g (0.2 moles) of ε-caprolactam with 70 ml of water and 32 g (0.4 moles) of a 50% NaOH solution in water and heated for 3 hours at 100° C. A slurry is prepared by mixing 111.44 g (0.4 moles) of 96% pure 2-chloroethyl imino bis(methylene phosphonic acid) and 250 cc of water. 30 g (0.375 moles) of 50% NaOH solution in water diluted to 100 ml with water are gradually added to this slurry between 5 and 8° C. Solution 3 is prepared by diluting 98 g (1.225 moles) of a 50% NaOH solution with 250 ml of water. Solutions 2 and 3 are gradually added to Solution 1 under mixing between 8 and 10° C. The resulting mixture is then heated to about 100° C. for 5 hours. $^{31}$P NMR analysis of the crude reaction mixture shows 42.7% w/w of hexanoic acid 6-imino bis[ethyl 2-imino bis(methylene phosphonic acid)]; 28.5% w/w hexanoic acid 6-amino ethyl 2-imino bis(methylene phosphonic acid) and 13% w/w of 2-hydroxy ethyl imino bis(methylene phosphonic acid).

Thermal Stability Assessment.

This is a test to assess the thermal stability of phosphonates in the presence of synthetic North Sea water. The test is carried out by submitting mixtures of North Sea water and phosphonates stabilized at pH 5.5 to a one week heating at 140° C. The thermal degradation is determined by $^{31}$P NMR analysis. The results give the percentage by weight of product which is decomposed after the treatment.

Test details are as follows:

- prepare an aqueous solution containing 20% of active acid phosphonate (AA) at pH 5.5 (solution 1);
- prepare synthetic North Sea water having a pH of 5.5 (solution 2);
- prepare a sample of 1% active acid phosphonate by mixing 1 g of solution 1 with 19 g of solution 2;
- put the sample so prepared in an oven at 140° C. for one week; and
- analyze the sample, after the heat treatment, for thermal decomposition by means of $^{31}$P NMR spectroscopy.

Brine/Sea Water Compatibility.

This test assesses sea water compatibility of the phosphonates added at: 100; 1000; 10000; and 50000 ppm to North Sea water after 22 hours at 90° C. Calcium left in solution is measured by ICP.

Test details are as follows:

- prepare synthetic North Sea water at pH 5.5;
- add the phosphonate at 100, 1000, 10000 and 50000 ppm active acid to the synthetic North Sea water solution;
- prepare 5 blank solutions made by mixing the required amount of distilled water with North Sea water to obtain the same dilution as obtained by the addition of 1, 100, 1000, 10000 and 50000 ppm active acid phosphonate to the synthetic North Sea water solution;
- the phosphonate samples with the respective phosphonates at the 4 concentrations as well as the 5 blanks are stored in an oven at 90° C. for a period of 22-24 hours;
- upon completion of the test, the samples are observed visually;
- after completion of the test, the pH values are being carefully monitored and 50 ml are drawn from each sample, filtered through a 40 μm Millipore filter and stabilized at pH<2 by addition of 37% aqueous hydrochloric acid;
- Ca tolerance values are calculated as follows:

$$\% \text{ Ca tolerance} = \frac{V_1}{V_0} \times 100$$

where $V_0$=ppm Ca found in the blank solution; and
where $V_0$=ppm Ca found in the blank solution; and
$V_1$=ppm Ca found in the solution with the phosphonate.

Barium Sulphate Scale Inhibition.

This is a static test to evaluate the efficiency of phosphonates in preventing barium and strontium scale inhibition in oil field scaling conditions. The test is carried out by determining the amount of $BaSO_4$ and $SrSO_4$ that has precipitated after 22 hours at 90° C. in a 50/50 mixture of synthetic North Sea water and Formation water containing the phosphonates to be tested at 5 different concentrations. The amount of soluble Ba and Sr ions is determined by ICP. The results stand for the minimum phosphonate concentration for 100% barium sulphate scale inhibition or give the scale inhibition at 100 ppm loading of phosphonate.

Test Details are as Follows:

Synthetic North Sea Water:

| Salts | mmol/l |
|---|---|
| NaCl | 420.1 |
| $CaCl_2 \cdot 2H_2O$ | 10.08 |
| $MgCl_2 \cdot 6H_2O$ | 54.32 |
| KCl | 8.7 |
| $Na_2SO_4 \cdot 10H_2O$ | 25.8 |
| $NaHCO_3$ | 2.21 |

Formation Water:

| Salts | mmol/l |
|---|---|
| NaCl | 1313 |
| $CaCl_2 \cdot 2H_2O$ | 77.75 |
| $MgCl_2 \cdot 6H_2O$ | 19.74 |
| KCl | 11 |
| $BaCl_2 \cdot 2H_2O$ | 1.82 |
| $SrCl_2 \cdot 6H_2O$ | 7.53 |

- synthetic North Sea and Formation water are prepared having a pH of 6. These water solutions are preheated at 90° C. before starting the test. An acetic acid/sodium acetate buffer is prepared and added to the North Sea water in order to give the required pH;
- add to a glass bottle the required amount of scale inhibitor to obtain the test concentrations (15, 30, 50, 70 and 100 ppm active phosphonic acid) of the scale inhibitor in the final test mixture;
- to this glass bottle, add 50 ml of North Sea water while stirring. Then add to this glass bottle 50 ml of Formation water;
- also prepare one blank solution by mixing 50 ml of North Sea water with 50 ml of Formation water;
- put the sample bottles in an oven for 22 hours at 90° C.;
- after 22 hours, take 3 ml of each test solution from the surface, filter through a 0.45 μm Millipore filter and add to a stabilizing solution. The samples are then analyzed by ICP for Ba and Sr;
- the phosphonate efficiencies as $BaSO_4$ and $SrSO_4$ scale inhibition are calculated as follows:

$$\%\ \text{Scale inhibition} = \frac{V_1 - V_0}{V_2 - V_0} \times 100$$

where $V_0$=ppm Ba (or Sr) found in the blank solution;

$V_1$=ppm Ba (or Sr) found in the solution with the inhibitor;

$V_2$=ppm Ba (or Sr) present in the Formation water.

Testing Method for Calcium Carbonate Scale Inhibition.

This is a static test to evaluate the efficiency of phosphonates in preventing calcium carbonate scale inhibition in industrial water treatment conditions. The test is carried out by determining the amount of $CaCO_3$ that has precipitated after 22 hours at 50° C. in a 50/50 mixture of cationic and anionic waters with the test phosphonates at 5 different concentrations. The amount of soluble Ca ions is analyzed by titration. Result indicates the % Ca scale inhibition provided by the 5 phosphonate concentrations. Reported results give the minimum phosphonate concentration for 100% calcium carbonate scale inhibition.

Test Details are as Follows:

Cationic Water Composition

| Salt | g/l |
|---|---|
| $CaCl_2 \cdot 2H_2O$ | 1.76 |

Anionic Water Composition

| Salt | g/l |
|---|---|
| NaHCO3 | 2.02 |

- Cationic and anionic waters are prepared at pH 9. 100 ml of buffer are added to the anionic water before bringing water to its final 1 liter final volume.
- Prepare a 1000 ppm phosphonate solution in water at pH 9.
- Add to a glass bottle the required amount of the scale inhibitor mother phosphonate solution to obtain the test concentration (1, 2, 2.5, 3 and 3.5 ppm active phosphonic acid) of the scale inhibitor in the final test mixture.
- To this glass bottle add 50 ml of anionic water while stirring and then 50 ml of cationic water while stirring.
- Put the sample bottles in an oven for 22 hours at 50° C.
- After 22 hours, take 50 ml of each test solution from the surface, filter through a 0.45 μm Millipore filter, measure and note the weight of the solution (Wtsam) and acidify to pH 1 with an HCl solution. Measure and note the HCl solution weight added (Wta).
- Analyze Ca by titration (Caf).
- The phosphonate efficiency as $CaCO_3$ scale inhibition is then calculated using the following equation:

$$\%\ CaCO_3\ \text{scale inhibition} = (Cat - Cab) \times 100) \div (Cai - Cab)$$

where

- Cat=Calcium remaining in solution of the test sample, where the dilution with acid has been corrected
- Cab=Calcium remaining in the blank where no phosphonate was added.
- Cai=Total calcium present in the original test sample
- Cat=(Caf)×(Wta)/Wtsam Peroxide Stabilization Procedure In a 250 ml glass bottle filled with 200 ml deionised water stabilized at 40° C. add the following ingredients: 0.4 g of iron, 35 ppm of the tested bleach stabilizer, 0.53 g of sodium bicarbonate, 0.42 g of sodium carbonate, 0.14 g of sodium perborate tetrahydrate and 0.06 g of tetra-acetyl ethylene diamine (TAED). Dissolve these ingredients in the water by using an ultrasonic bath. After one minute of such treatment the bottle is transferred to the water bath set at 40° C. and samples (10 ml each) are taken from the test bottle 2, 6, 10, 15, 20 and 30 minutes thereafter. To these samples are added 10 ml of 1M potassium iodide and 10 ml of 20% aqueous sulphuric acid before immediate titration with a standardized 0.01N thiosulphate solution.

Clay Dispersion.

This test is used to determine and compare the effectiveness of the phosphonate agents of this invention.

A one liter 0.15% w/w solution of the selected phosphonate is prepared in tap water. The solution pH is brought to 11.5 by addition of a 50% sodium hydroxide aqueous solution. Kaolin (1 g) is added and the liquid is agitated, at ambient temperature, till a homogeneous suspension is obtained. The suspension is then introduced in an Imhoff cone. Gradually a second phase appears at the bottom of the cone and its level is recorded at regular intervals (5, 15, 30, 60 and 120 minutes). The aspect and color of the two phases were also recorded at the same intervals. The percentage of dispersion provided by the tested product after 120 minutes is calculated as follows by reference to a blank test which does not contain a phosphonate.

% Dispersion=100−(level of the bottom phase (in ml)×100/level of the bottom phase in the blank (in ml)).

Phosphonate samples for use in the method of this invention were performance tested by means of the foregoing testing procedures. The performance data illustrated in the Application Examples were as follows.

Example I

| N° Phosphonate | Ba Scale(***) Inhibition | Ca Tolerance in % | | | |
|---|---|---|---|---|---|
| | | 100 | 1000 | 10000 | 50000 |
| 1. 2-aminoethoxy ethanol PIBMPA(*) | 15 ppm full scale | 100 | 95 | 94 | 86 |
| 2. 11-amino undecanoic acid PIBMPA | 75% @100 ppm | 100 | 92 | 32 | 6 |
| 3. Glycine PIBMPA | 100% @100 ppm | 100 | 94 | 32 | 91 |
| 4. 6-Amino hexanoic acid PIBMPA | 15 ppm full scale | 100 | 96 | 63 | 100 |
| 5. Glycine EIBMPA(*) | 100% @100 ppm | | | | |
| 6. Amino EIBMPA | 100% @100 ppm | 100 | 98 | 38 | 63 |
| 7. Dequest 2066A(****) | 15 ppm full scale | 100 | 89 | 24 | 100 |
| 8. AMODHMPA(*****) | 30 ppm full scale | 99 | 83 | 21 | 100 |
| 9. HEIBMPA(******) | 30 ppm full scale | 100 | 79 | 100 | 100 |
| 10. PEI IBMPA I(+) | 30 ppm full scale | 95 | 93 | 70 | 95 |
| 11. PEI IBMPA II(++) | 30 ppm full scale | 89 | 85 | 38 | 95 |

(*) PIBMPA stands for propyl imino bis (methylene phosphonic acid)
(**) EIBMPA stands for ethyl imino bis (methylene phosphonic acid)
(***) expressed as:
ppm phosphonate needed for 100% $BaSO_4$ scale inhibition;
or
% scale inhibition for 100 ppm phosphonate.
(****) is diethylene triaminopentamethylene phosphonate.
(*****) AMODHMPA stands for 4-aminomethyl 1,8-octane diamine hexa(methylene phosphonic acid)
(******) HEIBMPA stands for 2-hydroxy ethyl imino bis (methylene phosphonic acid
(+)PEI IBMPA stands for polyethylene imine poly (propyl imino bis (methylene phosphonic acid))with molar ratio 3-chloro propyl imino bis (methyelene phosphonic acid)/PEI = 0.75
(++)PEI IBMPA stands for polyethylene imine poly(propyl imino bis(methylene phosphonic acid))with molar ratio 3-chloro propyl imino bis (methyelene phosphonic acid)/PEI = 1.14

Example II

| N° | Phosphonate | Ca Scale (***) Inhibition |
|---|---|---|
| 1. | 2-aminoethoxy ethanol PIBMPA | 2 ppm full scale |
| 2. | 11-amino undecanoic acid PIBMPA | 2 ppm full scale |
| 3. | Glycine PIBMPA | 2 ppm full scale |
| 4. | 6-Amino hexanoic acid PIBMPA | 2 ppm full scale |
| 5. | Amino EIBMPA | 2 ppm full scale |

-continued

| N° | Phosphonate | Ca Scale (***) Inhibition |
|---|---|---|
| 7. | Dequest 2066A | 2 ppm full scale |

A series of phosphonate inhibitors were tested for thermal stability thereby using the method set forth above. The testing results were as follows.

Example III

| Test N° | Phosphonate | Thermal Stability at 140° C. 1 week Decomposition in % |
|---|---|---|
| 1. | 2-aminoethoxy ethanol PIBMPA | 17 |
| 2. | 11-amino undecanoic acid PIBMPA | 35 |
| 3. | Glycine PIBMPA | 27 |

-continued

| Test N° | Phosphonate | Thermal Stability at 140° C. 1 week Decomposition in % |
|---|---|---|
| 4. | 6-Amino hexanoic acid PIBMPA | 38 |
| 5. | Glycine EIBMPA | 13 |
| 7. | Dequest 2066A | 24 |
| 8. | AMODHMPA | 8.8 |
| 9. | HEIBMPA | 19 |

A series of phosphonates were tested for peroxide stabilization thereby using the method set forth above. The testing results were as follows.

Example IV

| Phosphonate | Time (min) | % remaining act.oxygen |
|---|---|---|
| None | 0 | 100 |
| | 2 | 92 |
| | 6 | 80 |
| | 10 | 71 |
| | 15 | 61 |
| | 20 | 53 |
| | 30 | 53 |
| +35 ppm Dequest 2066 | 0 | 100 |
| | 2 | 100 |
| | 6 | 99 |
| | 10 | 97 |
| | 15 | 95 |
| | 20 | 94 |
| | 30 | 90 |
| +45.5 ppm 6-amino hexanoic acid PIBMPA | 0 | 100 |
| | 2 | 88 |
| | 6 | 83 |
| | 10 | 79 |
| | 15 | 73 |
| | 20 | 71 |
| | 30 | 67 |
| +35 ppm Imino bis(EIBMPA) | 0 | 100 |
| | 2 | 100 |
| | 6 | 93 |
| | 10 | 91 |
| | 15 | 91 |
| | 20 | 90 |
| | 30 | 89 |
| +17.5 ppm Imino bis(EIBMPA) | 0 | 100 |
| | 2 | 100 |
| | 6 | 97 |
| | 10 | 96 |
| | 15 | 96 |
| | 20 | 94 |
| | 30 | 94 |
| +35 ppm of 6-amino hexanoic acid EIBMPA | 0 | 100 |
| | 2 | 100 |
| | 6 | 98 |
| | 10 | 98 |
| | 15 | 96 |
| | 20 | 95 |
| | 30 | 93 |

Example V

Clay dispersion

| Time | Blank test | | 6-Amino hexanoic acid PIBMPA | | Glycine PIBMPA | |
|---|---|---|---|---|---|---|
| (Min) | ml(1) | (2) | ml(1) | (2) | ml(1) | (2) |
| 5 | 6 | cloudy | 0.15 | cloudy | 0.4 | cloudy |
| 15 | 7 | cloudy | 0.4 | cloudy | 0.6 | cloudy |
| 30 | 6 | cloudy | 0.55 | cloudy | 0.9 | cloudy |
| 60 | 6 | clear | 0.8 | cloudy | 1.1 | cloudy |
| 120 | 6 | clear | 1 | cloudy | 1.2 | cloudy |
| % Dispersion | | 0.0 | | 82 | | 78 |

| Time | Blank test | | Glycine EIBMPA | | 2-(2-Amino ethoxy)ethanol PIBMPA | |
|---|---|---|---|---|---|---|
| (Min) | ml(1) | (2) | ml(1) | (2) | ml(1) | (2) |
| 5 | 6 | cloudy | 0.2 | cloudy | 0.5 | cloudy |
| 15 | 7 | cloudy | 0.5 | cloudy | 0.75 | cloudy |
| 30 | 6 | cloudy | 0.7 | cloudy | 1.0 | cloudy |
| 60 | 6 | clear | 1.0 | cloudy | 1.0 | cloudy |
| 120 | 6 | clear | 1.2 | cloudy | 1.4 | cloudy |
| % Dispersion | | 0.0 | | 78 | | 74 |

| Time | Blank test | | Imino bis (EIBMPA) | | 11-Amino undecanoic Acid PIBMPA | |
|---|---|---|---|---|---|---|
| (Min) | ml(1) | (2) | ml(1) | (2) | ml(1) | (2) |
| 5 | 6 | cloudy | 0.2 | cloudy | 0.4 | cloudy |
| 15 | 7 | cloudy | 0.3 | cloudy | 0.7 | cloudy |
| 30 | 6 | cloudy | 0.5 | cloudy | 1.0 | cloudy |
| 60 | 6 | clear | 0.7 | cloudy | 1.2 | cloudy |
| 120 | 6 | clear | 0.9 | cloudy | 1.3 | cloudy |
| % Dispersion | | 0.0 | | 80 | | 71 |

The invention claimed is:

1. A method of scale inhibition in aqueous medium due to metal ion interferences comprising adding to the water of from 0.1 to 100000 parts per million (ppm) of a phosphonate compound selected from the group consisting of:

(a) a phosphonate compound of the general formula:

T-B wherein B is a phosphonate containing moiety having the formula:

$—X—N(W)(ZPO_3M_2)$ wherein X is selected from the group consisting of $C_2$-$C_{50}$ linear, branched, cyclic or aromatic hydrocarbon moiety, optionally substituted by a $C_1$-$C_{12}$ linear, branched, cyclic, or aromatic group, which moiety and/or which group can be optionally substituted by OH, COOH, F, OR' and SR' moieties, wherein R' is a $C_1$-$C_{12}$ linear, branched, cyclic or aromatic hydrocarbon moiety; and $[A-O]_x$-A wherein A is a $C_2$-$C_9$ linear, branched, cyclic or aromatic hydrocarbon moiety and x is an integer from 1 to 200;

Z is a $C_1$-$C_6$ alkylene chain;

M is selected from the group consisting of alkali, earth alkali and ammonium ions and from protonated amines;

W is selected from the group consisting of H, $ZPO_3M_2$ and $[V—N(K)]_nK$, wherein V is selected from: a $C_2$-$C_{50}$ linear, branched, cyclic or aromatic hydrocarbon moiety, optionally substituted by $C_1$-$C_{12}$ linear, branched, cyclic or aromatic groups, which moieties and/or groups are optionally substituted by OH, COOH, F, OR' or SR' moieties wherein R' is a $C_1$-$C_{12}$ linear, branched, cyclic or aromatic hydrocarbon moiety; and from $[A-O]_x$-A wherein A is a $C_2$-$C_9$ linear, branched, cyclic or aromatic hydrocarbon moiety and x is an integer from 1 to 200; and K is $ZPO_3M_2$ or H and n is an integer from 0 to 200;

and wherein T is a moiety selected from the group consisting of:

MOOC—X—N(U)—; (i)

MOOC—$C(X^2)_2$—N(U)—; (ii)

MOOC—X—S—; (iii)

$[X(HO)_{n'}(N—U)_{n''}]_{n'''}$—; (iv)

U—N(U)—$[X—N(U)]_{n'''}$—; (v)

D-S—; (vi)

CN—; (vii)

MOOC—X—O—; (viii)

MOOC—$C(X^2)_2$—O—; (ix)

NHR"—; and (x)

$(DCO)_2$—N—; (xi)

wherein M, Z, W and X are as defined above; U is selected from the group consisting of linear, branched, cyclic or aromatic $C_1$-$C_{12}$ hydrocarbon moieties, H and X—N (W) ($ZPO_3M_2$); $X^2$ is independently selected from the group consisting of H, linear, branched, cyclic or aromatic $C_1$-$C_{20}$ hydrocarbon moieties, optionally substituted by $C_1$-$C_{12}$ linear, branched, cyclic or aromatic hydrocarbon groups, optionally substituted by OH, COOH, R'O, R'S and/or $NH_2$ moieties; n', n" and n'" are independently selected from integers of from 1 to 100; D and R" are independently selected from the group consisting of $C_1$-$C_{50}$ linear, branched, cyclic or aromatic hydrocarbon moieties, optionally substituted by a $C_1$-$C_{12}$ linear, branched, cyclic, or aromatic group, which moiety and/or which group can be optionally substituted by OH, COOH, F, OR' and SR' moieties, wherein R' is a $C_1$-$C_{12}$ linear, branched, cyclic or aromatic hydrocarbon moiety; and A'O-$[A\text{-}O]_x$-A wherein A is a $C_2$-$C_9$ linear, branched, cyclic or aromatic hydrocarbon moiety, x is an integer from 1 to 200 and A' is selected from the group consisting of $C_1$-$C_{50}$ linear, branched, cyclic or aromatic hydrocarbon moiety, optionally substituted by a $C_1$-$C_{12}$ linear, branched, cyclic, or aromatic group, which moiety and/or which group can be optionally substituted by OH, COOH, F, OR' and SR' moieties, wherein R' has the meaning given above; with the further proviso that D can also be represented by H;

(b) linear or branched hydrocarbon moieties having from 6 to $2\cdot10^6$ carbon atoms containing amino groups substituted by alkylene phosphonic acid substituents and/or —X—N(W)($ZPO_3M_2$) with respect to the hydrocarbon moiety, in either terminal or branched positions whereby the molar ratio of the amine moieties to the number of carbon atoms in the hydrocarbon chain is in the range of from 2:1 to 1:40 whereby at least 30% of the available NH functionalities have been converted into the corresponding aminoalkylene phosphonic acid or/and into X—N(W)($ZPO_3M_2$) substituted groups; and wherein the alkylene moiety is selected from $C_1$-6; and X, W, Z and M have the same meaning as given above.

2. The method in accordance with claim 1 wherein the phosphonic acid compound is added in an amount of from 1 to 10000 ppm.

3. The method in accordance with claim 1 wherein in component (a) the reaction partner T is selected from the group consisting of (i), (ii), (iv), (v), and (x).

4. The method in accordance with claim 3 wherein the reaction partner T is selected from the group consisting of:

(i): caprolactam or 6-amino hexanoic acid; 2-pyrrolidone or 4-amino butanoic acid; and lauryl lactam or 12-amino dodecanoic acid;

(ii): glutamic acid; methionine; lysine; aspartic acid; phenylalanine; glycine; and threonine;

2-ethanol amine; 6-amino hexanol; 4-amino butanol; di-(2-ethanolamine); dipropanolamine; 2-(2-aminoethoxy) ethanol; and 3-propanol amine;

diaminotoluene; 1,6-hexamethylene diamine; 1,4-butane diamine; and 1,2-ethylene diamine; and (x): phthalimide; succinimide; and maleimide.

5. The method in accordance with claim 1 wherein in component (a) the reaction partner T is selected from the group consisting of (iii), (vi), (viii) and (ix).

6. The method in accordance with claim 5 wherein the reaction partner T is selected from the group consisting of:

(iii): thioglycolic acid; and cysteine;

(vi): methylthiol; ethylthiol; propylthiol; pentylthiol; hexylthiol; octylthiol; thiophenol; thionaphthol; decylthiol; and dodecylthiol;

3-hydroxy propanoic acid; 4-hydroxy butanoic acid; 5-hydroxy pentanoic acid; and 2-hydroxy acetic acid; and (ix): tartaric acid; hydroxysuccinic acid; and $\alpha$-hydroxy isobutyric acid.

7. The method in accordance with claim 1 wherein the structural elements of T are selected from the group consisting of: $X^2$ is H or $C_1$-$C_{10}$; n', n" are independently 1-25; n'" is 1-50; R" is $C_1$-$C_{16}$ or A'O-$[A\text{-}O]_x$-A; D is H, $C_1$-$C_{16}$ or A'O-$[A\text{-}O]_x$-A, wherein for both, R" and D independently, A is $C_2$-$C_4$ and x is 1-100; X is $C_2$-$C_{12}$i and Z is $C_1$-$C_3$.

8. The method in accordance with claim 1 wherein the hydrocarbon chain in component (b) containing amino groups is selected from: poly(amino) alkanes;

poly(allyl) amines;

poly(vinyl amines); and polyethylene imines), branched or linear or combinations thereof whereby the alkylene phosphonic acids are represented by $C_{1\text{-}6}$ phosphonic acid moieties and whereby X is $C_2$-$C_{30}$ or $[A\text{-}O]_x$-A.

9. The method in accordance with claim 1 wherein component (b) is selected from the group of:

4-aminomethyl 1,8-octane diamine hexa(methylene phosphonic acid);

4-aminomethyl 1,8-octane diamine hexa(alkylene imino bis(methylene phosphonic acid));

poly[vinylamine bis(methylene phosphonic acid)];

polyethylene imine poly(alkylene imino bis(methylene phosphonic acid));

polyethylene imine poly(methylene phosphonic acid);

poly[vinylamine bis(alkylene imino bis(methylene phosphonic acid))]; and poly[vinylamine bis(methylene phosphonic acid)].

10. A method of use for a phosphonate compound according to claim 1 for deactivating metal ions in an aqueous medium, comprising the step of adding the phosphonate compound to the aqueous medium in an amount of from 0.1 to 100000 ppm.

11. The method according to claim 10, where the phosphonate compound acts as a scale inhibitor, dispersant, exfoliating agent, sequestering agent or stabilizer.

12. The method according to claim 10, where the aqueous solution is applied in oil production, industrial water treatment, reverse osmosis, or paper pulp treatment.

* * * * *